United States Patent [19]
Seidler

[11] Patent Number: 5,950,690
[45] Date of Patent: Sep. 14, 1999

[54] LIQUID DOSAGE DISPENSERS

[75] Inventor: David Seidler, Forest Hills, N.Y.

[73] Assignee: Concept Workshop Worldwide, LLC, New York, N.Y.

[21] Appl. No.: 09/189,471

[22] Filed: Nov. 10, 1998

Related U.S. Application Data

[62] Division of application No. 08/671,549, Jun. 27, 1996, Pat. No. 5,836,359
[60] Provisional application No. 60/000,623, Jun. 30, 1995, and provisional application No. 60/005,346, Oct. 18, 1995.

[51] Int. Cl.$^6$ ..................................................... B67D 5/00
[52] U.S. Cl. ............................... 141/23; 141/94; 222/47; 222/309
[58] Field of Search .................................. 141/22, 23, 25, 141/27, 94, 95, 380, 381; 222/41, 47, 48, 309

[56] References Cited

U.S. PATENT DOCUMENTS

| | | | |
|---|---|---|---|
| 14,524 | 3/1856 | Stull | 141/23 |
| 1,178,512 | 4/1916 | Garlock | 141/23 |
| 1,241,207 | 9/1917 | Gilbert | 141/23 |
| 2,129,144 | 9/1938 | Lancaster | 141/23 |
| 3,168,913 | 2/1965 | Eagles | 141/23 |
| 4,165,646 | 8/1979 | Shapiro | 222/309 |
| 4,445,626 | 5/1984 | Steffen et al. | 222/47 |
| 4,526,294 | 7/1985 | Hirschmann et al. | 222/47 |
| 4,962,868 | 10/1990 | Borchard | 222/309 |
| 4,964,534 | 10/1990 | Strazdins | 222/309 |
| 5,279,586 | 1/1994 | Balkwill | 222/309 |
| 5,582,598 | 12/1996 | Chanoch | 222/309 |

*Primary Examiner*—J. Casimer Jacyna
*Attorney, Agent, or Firm*—Kramer Levin; Naftalis & Frankel LLP

[57] ABSTRACT

A liquid dosage dispenser includes a bottle and a dispenser apparatus supported on the bottle having a housing extending into the bottle and a plunger device extending into the housing for longitudinal movement therein. The housing includes an opening through which liquid in the bottle can be drawn into the housing, with one of the housing and plunger device including a stop system of predetermined configuration and the other of the housing and plunger device including a follower for contacting the stop system. The plunger is rotatable with respect to the housing to align the follower with a desired portion of the stop system, with the follower and stop system, when aligned, allowing the plunger to be moved longitudinally along the housing until the follower contacts the stop system to draw a predetermined amount of liquid through the opening into the housing. The dispenser is removable from the bottle to allow the predetermined amount of liquid to be dispensed through the opening.

4 Claims, 12 Drawing Sheets

LIQUID DOSAGE DISPENSERS

This application is a division of application Ser. No. 08/671,549 filed on Jun. 27, 1996 entitled LIQUID DOSAGE DISPENSERS, now U.S. Pat. No. 5,836,359.

CROSS-REFERENCE TO RELATED PROVISIONAL APPLICATIONS

This application claims the benefit of U.S. Provisional Application Nos. 60/000,623 filed on Jun. 30, 1995 and 60/005,346 filed on Oct. 18, 1995.

BACKGROUND OF THE INVENTION

The present invention is directed generally to liquid dosage dispensers and, in particular, to a package which dispenses a selected precise amount of a liquid, such as medicine, in predetermined dosages. In addition, the dispenser may include a compliance indication with programmability features.

Medicine in liquid form is well known, as are systems which allow for measurement of particular dosages to different individuals. For example, a particular liquid cough medicine might have one dosage for young children, a second dosage for teenagers, and a third dosage for adults, to provide the appropriate benefits of the medicine for each age group.

A common form for measuring appropriate dosages includes providing a premarked dosage cup with lines or other indicia to indicate the appropriate dosage. Other liquid medicines may provide a spoon type device or eye dropper, again with indicia to allow a user to remove the appropriate dosage from a bottle, which is then dispensed into the user's mouth or a cup or the like.

Such systems for measuring dosages of medicine have proven cumbersome and may provide inaccurate dosages, resulting perhaps in either underdosing or overdosing.

In another situation, patients who are often required to take liquid medicine on a regular basis and their physicians would prefer using a compliance package which identifies the number of times or time of day that the medicine is taken, as well as to provide a precise measurement thereof.

The present invention provides an adjustable liquid dosage dispenser and a liquid compliance package with programmable dosage features which overcome the shortcomings of the prior art systems while providing desirable features of construction and ease of operation.

SUMMARY OF THE INVENTION

Generally speaking, in accordance with the present invention, a liquid dosage dispenser is provided. The liquid dosage dispenser includes a bottle for containing a liquid having an open neck and a dispenser apparatus supported on the neck. The dispenser apparatus includes a hollow housing extending into the bottle and a plunger device extending into the housing. The housing includes an opening through which liquid in the bottle can be drawn into the housing. One of the housing and plunger device includes a stop system of predetermined configuration for stopping longitudinal movement of the plunger. The other of the housing and plunger device include a follower for contacting the stop system. The plunger is rotatable with respect to the housing to align the follower with a desired portion of the stop system, with the follower and stop system, when aligned, allowing the plunger device to be moved longitudinally along the housing until the follower contacts the stop system to draw a predetermined amount of liquid through the opening into the housing. The dispenser apparatus is then removable from the bottle to permit the predetermined amount of drawn liquid to be dispensed through the opening.

In a first embodiment, the stop system includes a plurality of keyways of varying length which are dimensioned to permit precise drawing of a desired amount of liquid into the housing. In a second embodiment, the stop system includes a continuous slanted ramp to allow for a more fine adjustment of the dosages.

In another embodiment of the invention, the dispenser apparatus is fixed on the bottle. The housing and plunger device include cooperating valves and openings that permit liquid drawn into the housing to be dispensed through the plunger device. The stop system includes a trackway or path of predetermined configuration in which the follower rides during each longitudinal movement of the plunger with respect to the housing to provide a compliance package where an indication of each subsequent dosage is indicated and indexed.

Accordingly, it is an object of the present invention to provide an adjustable liquid dosage dispenser.

Another object of the present invention is to provide an adjustable liquid dosage dispenser which allows for precise measurement of desired dosages of a liquid.

A further object of the present invention is to provide a liquid dosage dispenser with a rotatable dial and plunger which allows for precise dosage measurement.

A still further object of the present invention is to provide a liquid compliance package with programmable dosage provisions.

Yet another object of present invention is to provide a liquid dosage dispenser which automatically indicates the particular sequence of dosages while providing an accurate dosage measurement.

Still other objects and advantages of the invention will in part be obvious and will in part be apparent from the specification.

The invention accordingly comprises the features of construction, combination of elements, and arrangement of parts which will be exemplified in the constructions hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

Figures 1, 2:
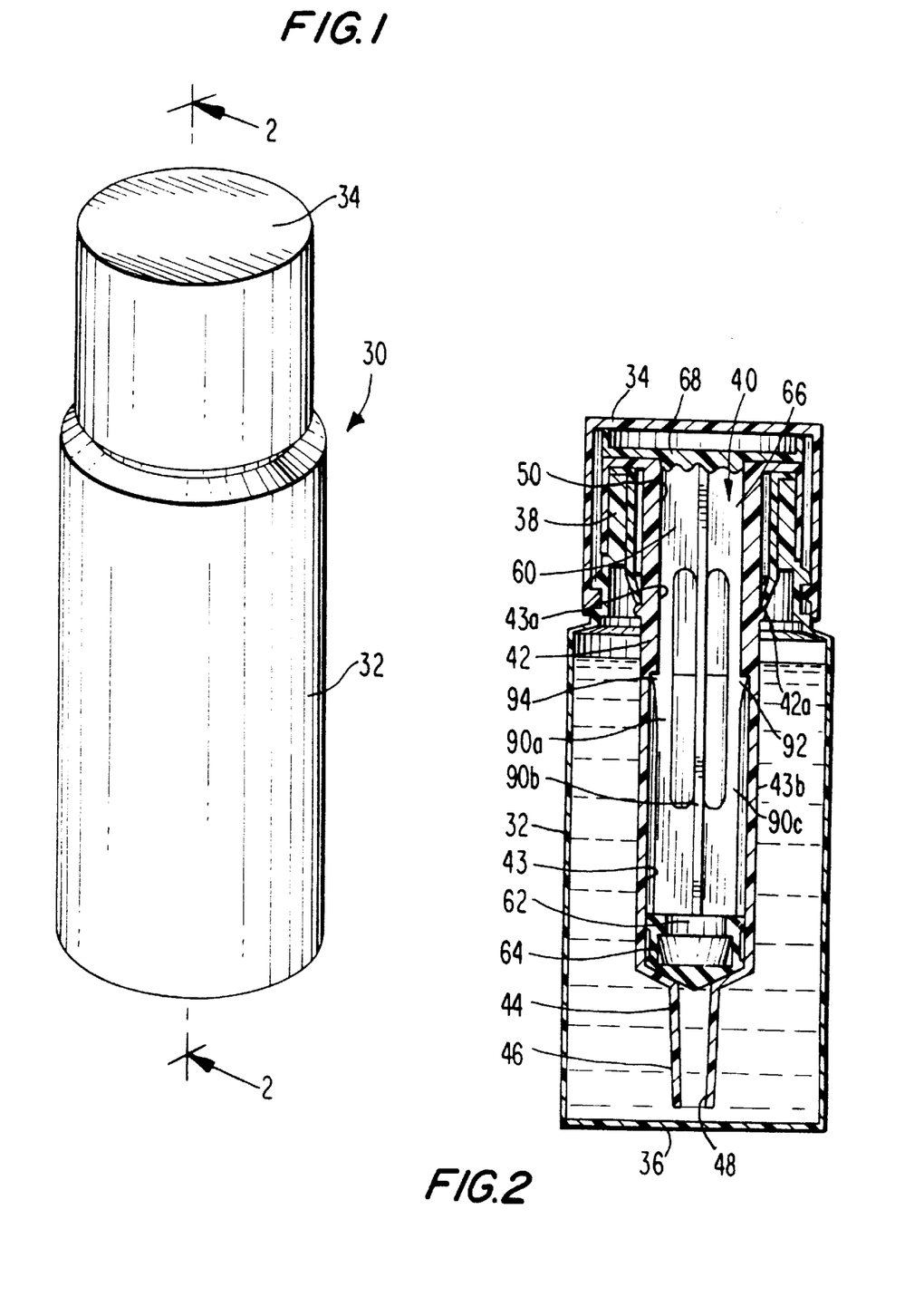
FIG. 1 is a perspective view of a liquid dosage dispenser constructed in accordance with a first embodiment of the present invention.
FIG. 2 is a sectional view taken along line 2—2 of FIG. 1.

Reference is first made to FIG. 1 of the drawings which depicts a container or dispenser package, generally indicated at 30, having a bottle 32 and a removable cap 34.

Referring now additionally to FIG. 2, it is noted that bottle 32 includes a closed bottom 36 and an open neck 38. It is also noted that cap 34 is removable from neck 38 and may be releasably secured thereto by a snap fit, threads, or the like. It is also noted that cap 34 may be a child resistant cap making it difficult for a child to remove cap 34 from bottle 32.

A dispenser apparatus shown generally at 40 is removably supported on neck 38 as hereinafter described in detail. Dispenser apparatus 40 includes a hollow housing 42 having a first end 44 defining an extension 46 having an opening 48, and a second open end 50. A plunger device 60 extends into the hollow portion 43 of housing 42. A first end 62 of plunger device 60 includes a rubber tip or other elastomeric material 64 which rides against the inner wall 43a of hollow portion 43 of housing 42 so that liquid can be drawn into housing 42 through opening 48 as will be described in detail hereinafter.

Second end 66 of plunger device 60 includes an enlarged area or panel 68 which can be grasped, rotated and pulled longitudinally through housing 42 to operate the dispenser of the present embodiment.

Referring now additionally to FIGS. 3 through 8 of the drawings, it is seen that panel 68 includes a window 70 which, when plunger device 60 is rotated in the direction of arrows A, can be selectively aligned with indicia 80 on a corresponding surface 52 of housing 42. Indicia 80 preferably represent the dosage amounts to be dispensed by the device, such as the 4 cc. indication depicted in FIG. 5. Indicia 80 may be raised to allow use by the blind.

Figure 3:
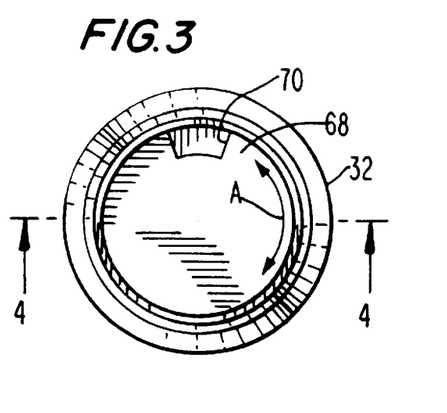
FIG. 3 is a top plan view of the dispenser depicted in FIGS. 1 and 2 shown with the outer cap removed.
Figure 4:
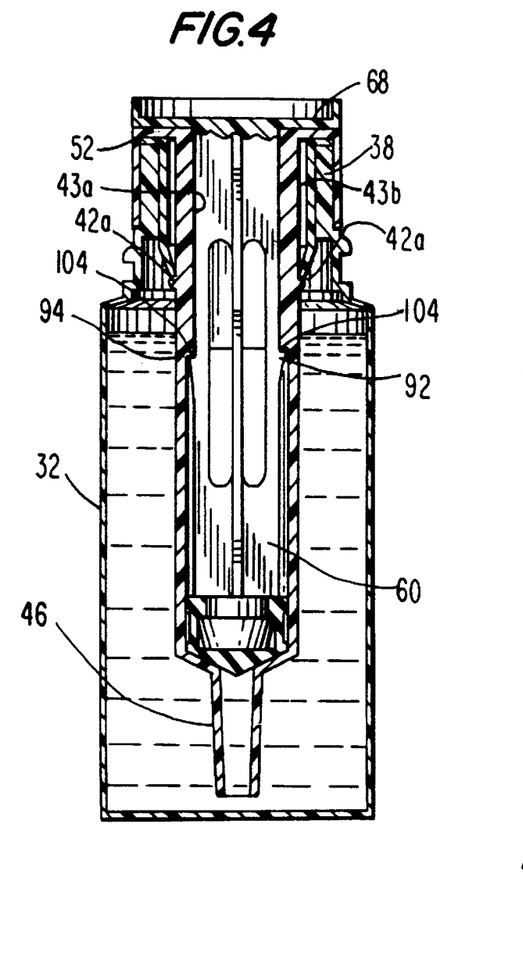
FIG. 4 is a sectional view taken along line 4—4 of FIG. 3.

In the position depicted in FIGS. 3 and 4, window 70 does not indicate an amount to be dispensed. Plunger 60, as depicted, may form a cross pattern in cross section defining four legs 90a through 90d. At least one of such legs 90a through 90d includes a projection, key or follower 92. In the embodiment depicted in FIGS. 1 through 6, two followers 92 and 94 are depicted, although it is noted that only one or more are required. It is also noted that the cross pattern is optional and many different forms or shapes of plungers can be used in the present invention so long as there is an ability to draw liquid into the housing.

Figures 11, 12:
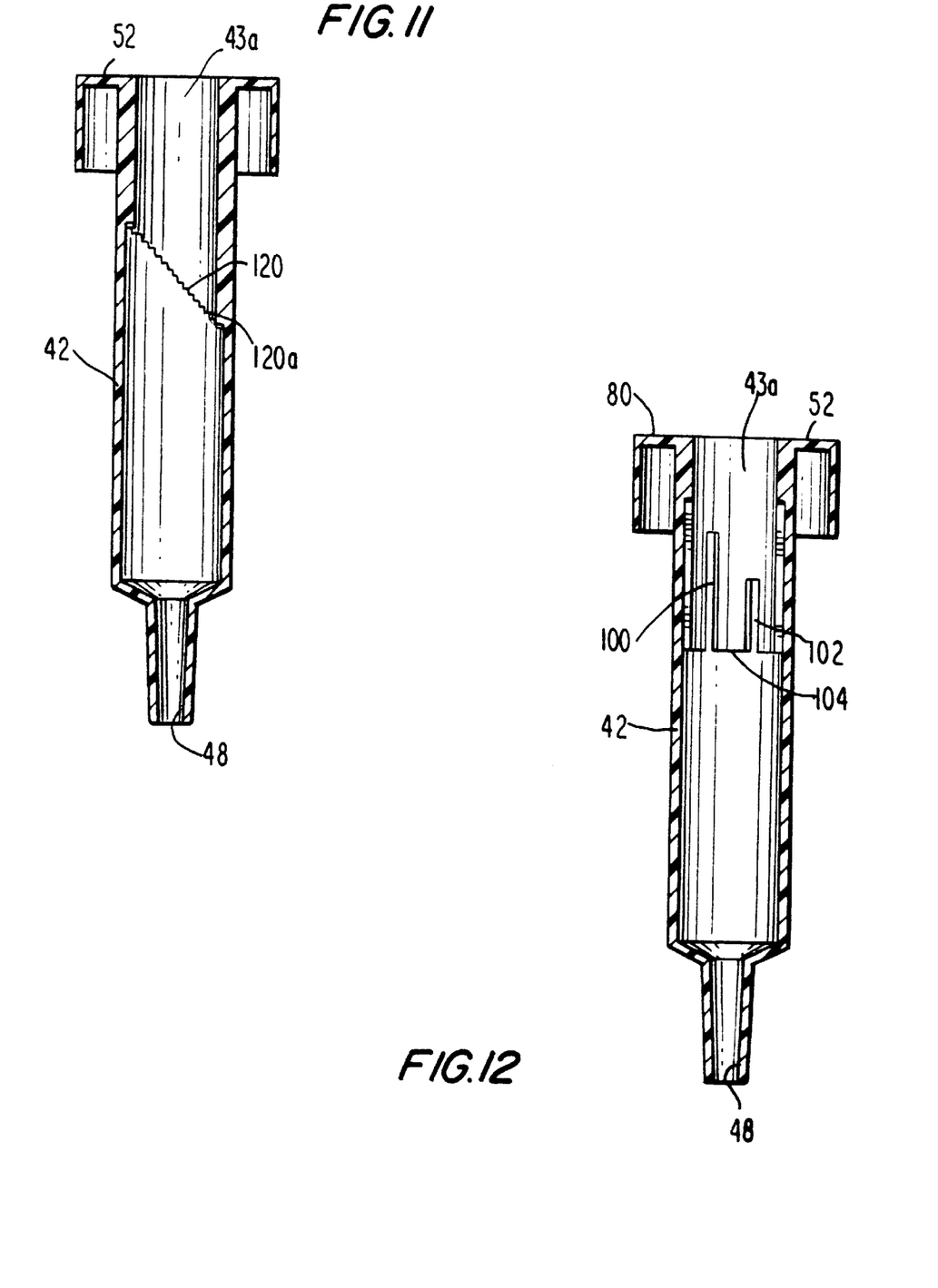
FIG. 11 is a sectional view of the tubular housing portion of the dispenser showing an alternative construction of the present invention.
FIG. 12 is a sectional view similar to FIG. 11 but showing separate formed keyways in the tubular housing member.

Inner surface 43a of housing 42 includes a stop system either in the form of an angular ramp 120 (FIG. 11) or in the form of passageways or keyways 100, 102 of varying lengths (FIG. 12) which, when aligned with an appropriate key 92 and/or 94 on plunger device 60, will allow longitudinal displacement of plunger device 60 with respect to housing 42. When keys 92 and/or 94 are appropriately aligned with corresponding keyways, window 70 will be appropriately aligned with corresponding indicia to indicate the amount of liquid to be drawn into housing 42 as plunger device 60 is moved longitudinally with respect to housing 42. The length of the keyway in which the follower rides or the longitudinal displacement of the plunger determines the amount of liquid drawn into the housing by the plunger. The angular ramp, which may be continuous or discontinuous, provides a plurality of dosage positions.

Figure 5:
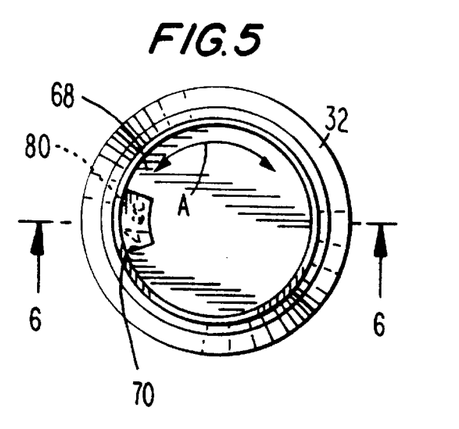
FIG. 5 is a top plan view similar to FIG. 3, but showing the plunger rotated to allow dispensing of a predetermined dosage.
Figure 6:
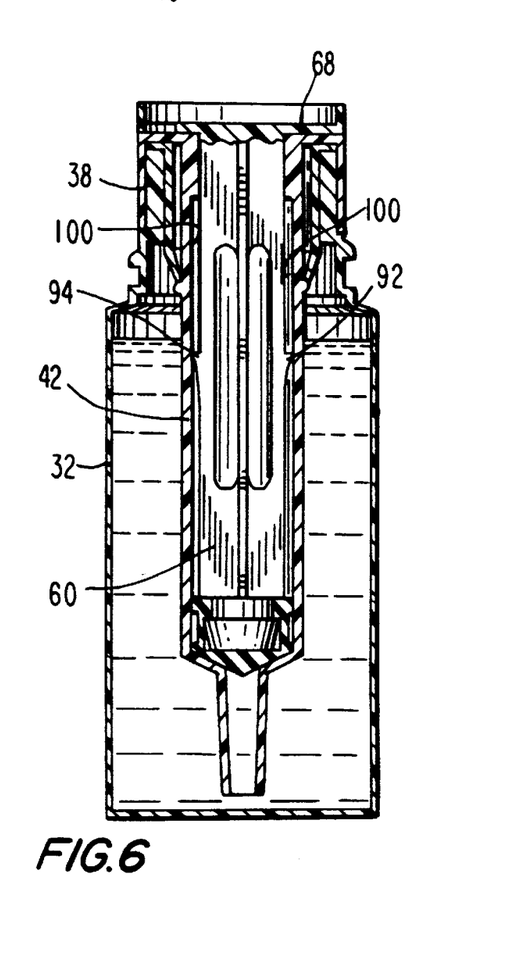
FIG. 6 is a sectional view taken along line 6—6 of FIG. 5.
Figures 7, 8:
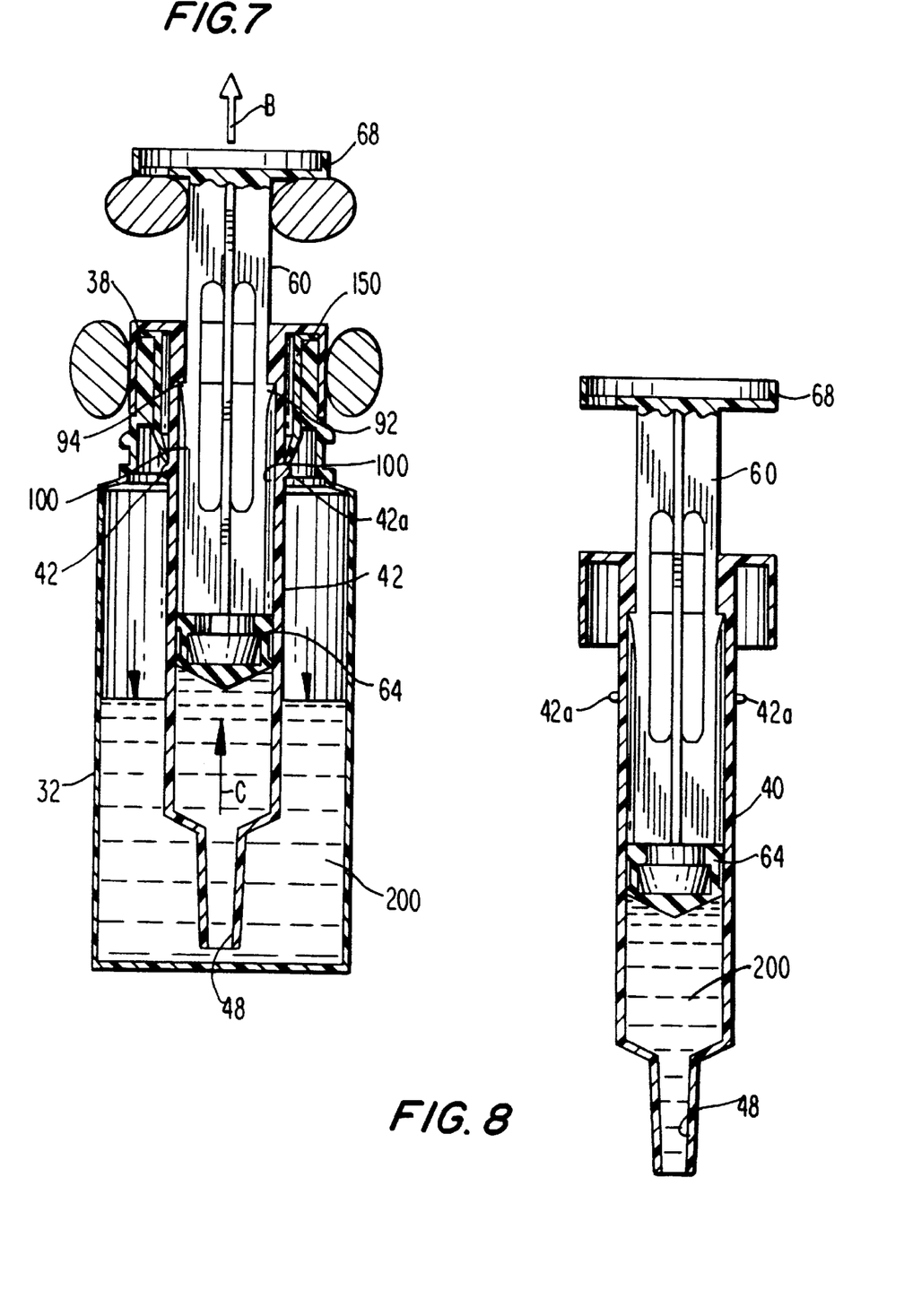
FIG. 7 is a sectional view similar to FIG. 6 but showing the plunger in a raised position prior to dispensing the product.
FIG. 8 is a sectional view of the dispenser shown filled with the appropriate dosage of product and withdrawn from the bottle.

In FIGS. 3 and 4, window 70 is not aligned with corresponding indicia 80. In this position, keys 92 and/or 94 contact enlarged regions 104 on inner surface 43a of housing 42, thereby preventing longitudinal movement of plunger device 60 with respect to housing 42. However, when plunger device 60 is rotated as shown in FIGS. 5 and 6 whereby a dosage is visible through window 70, keys 92 and/or 94 are aligned with corresponding keyways 100, for example, thereby allowing longitudinal movement of plunger device 60 in the direction of arrow B as shown in FIG. 7 with respect to housing 42. This action draws liquid 200 in bottle 32 through opening 48 in the direction of arrow C into housing 42. When keys 92 and/or 94 hit the top of keyway 100, longitudinal movement of plunger 68 with respect to housing 42 will be stopped and the precise amount of desired liquid, in this case 4 cc., will be drawn into housing 42.

An annular plastic or elastomeric wiper 150 is supported on neck 38 as depicted and cooperates with nibs 42a on outer wall 43b of housing 42, which may be in the form of individual projections or a continuous ring or the like, to releasably hold dispenser apparatus 40 on bottle 32 while plunger device 60 is rotated and moved longitudinally to its stop position. As shown in FIG. 7, the bottle can be grasped by two fingers and the plunger may be grasped by two fingers. Thereafter, additional force exerted in the direction of arrow B on dispenser apparatus 40 will allow withdraw of dispenser apparatus 40 from bottle 32 as best depicted in FIGS. 7 and 8, whereby thereafter the precise dosage of liquid 200 therein can be expelled and utilized. A venting slit may be provided adjacent to the wiper and nibs to allow for venting as the dispenser apparatus is removed.

Figures 9, 10:
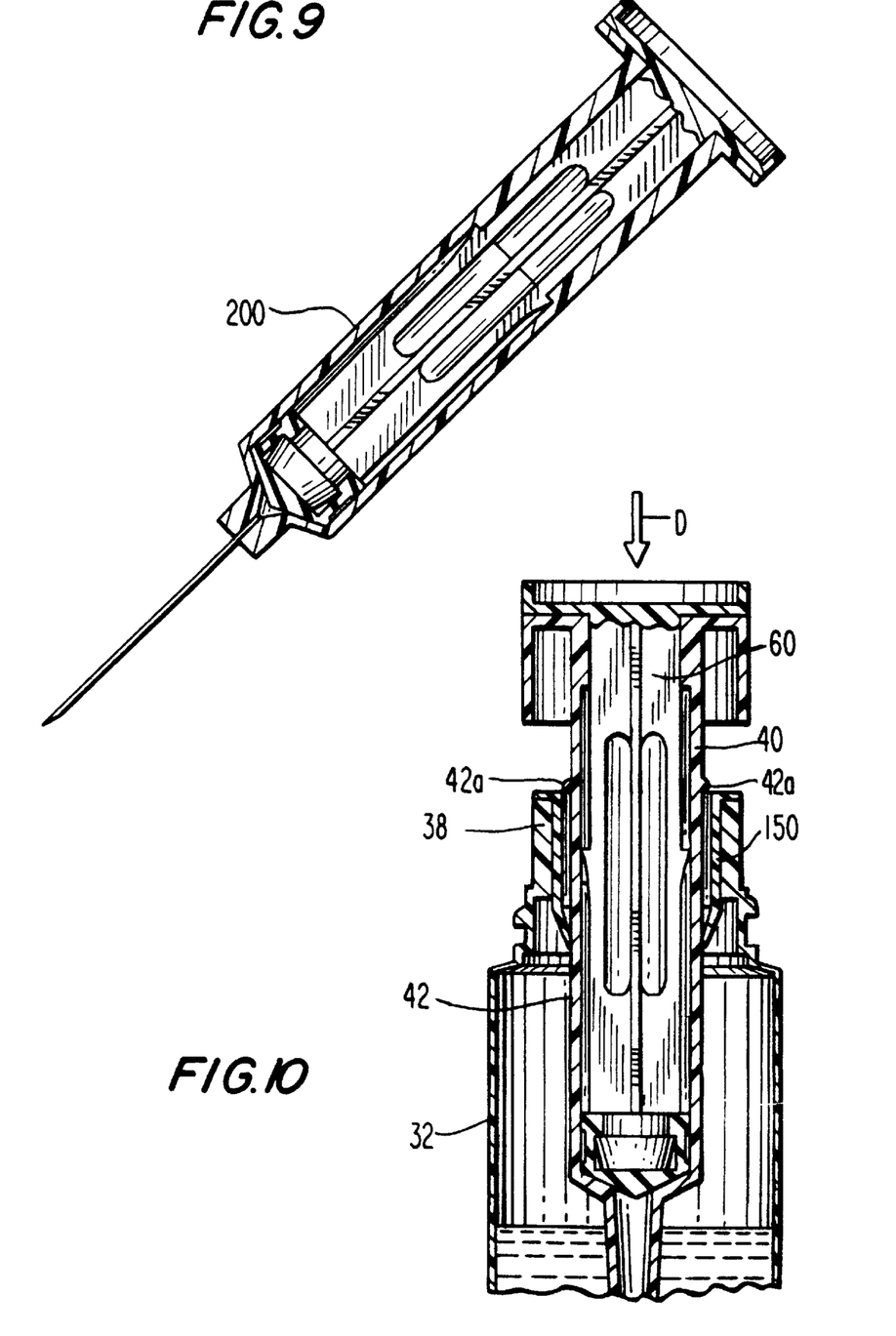
FIG. 9 is a sectional view of the dispenser apparatus of the present invention shown in use with a hypodermic needle.
FIG. 10 is a partial sectional view showing reinsertion of the dispenser apparatus into the bottle.

FIG. 10 depicts the manner of reinsertion of dispenser apparatus 40 into bottle 32 after dispensing has occurred. Housing 42 is inserted through neck 38 of bottle 32 and dispenser apparatus 40 is then pressed in the direction of arrow D whereby nibs 42a overcome the flexibility of wiper 150 to allow for reinsertion.

Figures 13, 14:
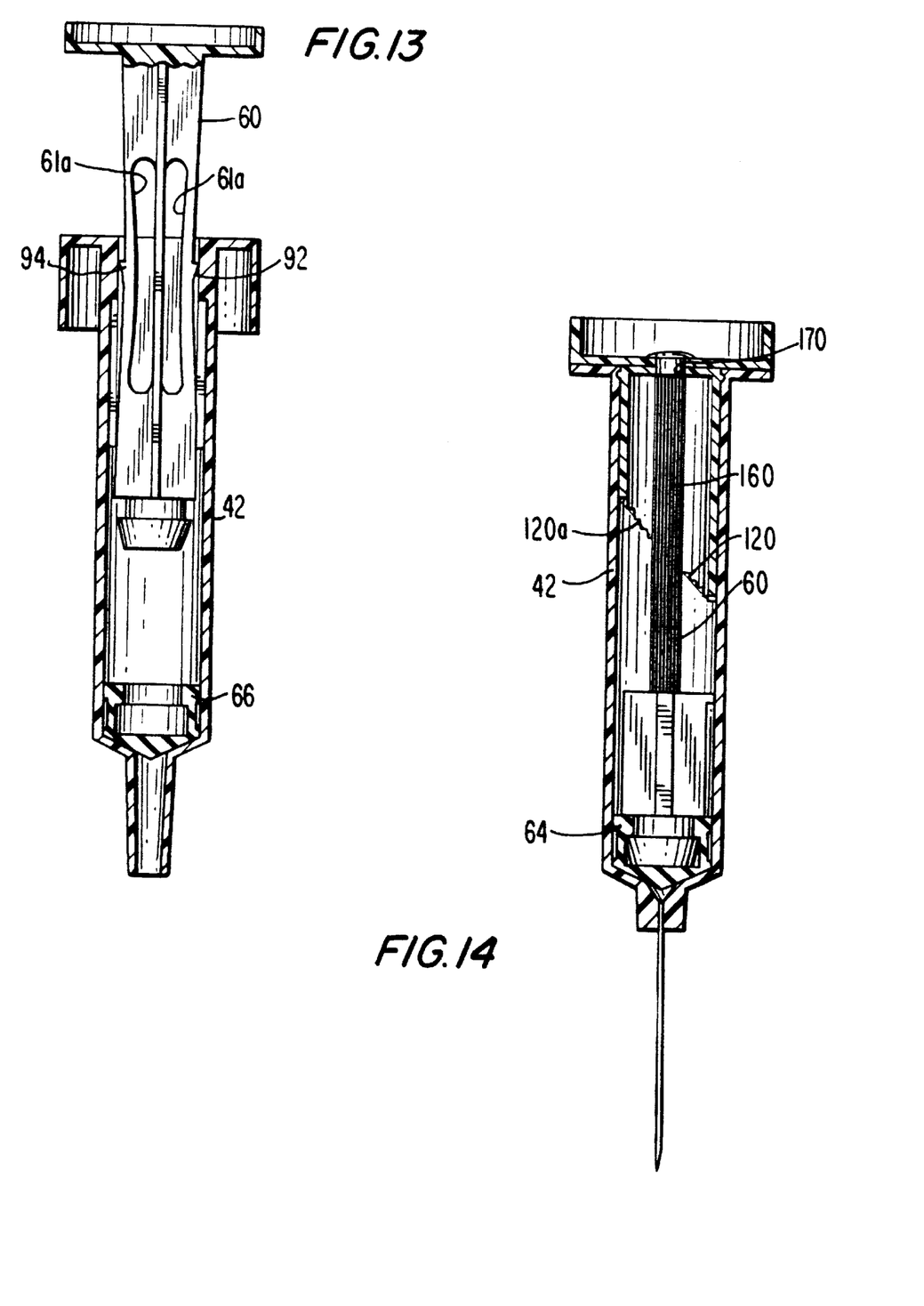
FIG. 13 is a sectional view showing the manner in which the plunger is inserted in the tubular housing member during manufacture of the device.
FIG. 14 is a sectional view of the dispenser in use with a hypodermic needle showing a preferred construction for the continuous ramp embodiment of the present invention.

FIG. 13 depicts the manner in which plunger device 60 is inserted in housing 42 during manufacture. In particular, it is noted that plunger device 60 includes open areas 61a adjacent keys 92 and 94 which allow inward flexing of the crosspieces of plunger 60 which carry the keys to allow plunger device 60 to be inserted into housing 42. It is noted that other forms of plunger devices may be utilized.

FIG. 9 depicts an embodiment of the present invention in the form of a hypodermic needle 200 wherein the dispenser apparatus including the housing and plunger device are utilized to allow for precise filling of needle 200 using the combination stop system and follower of the present invention. In this hypodermic needle embodiment, either the continuous ramp embodiment shown in FIG. 11 which is preferred for a hypodermic needle or the separate passageway embodiment shown in FIG. 12 can be utilized. However, it is noted with reference to FIG. 14, that when the continuous ramp embodiment is utilized either in connection with the regular dispenser shown in FIGS. 1 through 8 or the hypodermic needle embodiment shown in FIG. 9, the plunger device 60 preferably includes a plurality of serrations or the like 160 which mate with corresponding serrations 170 in housing 42 to prevent further rotation of plunger device 60 with respect to housing 42 as plunger 60 is moved longitudinally with respect to housing 42. It is also preferred in the slanted ramp embodiment to provide the ramp edge 120a with steps or serrations to prevent slipping of the follower during use.

Reference is now made to FIGS. 15 through 20 of the drawings which depict a container or dispenser package, generally indicated at 230 constructed in accordance with a further embodiment of the present invention. Dispenser package 230 includes a bottle 232 and a removable cap 234.

Figures 15, 16:
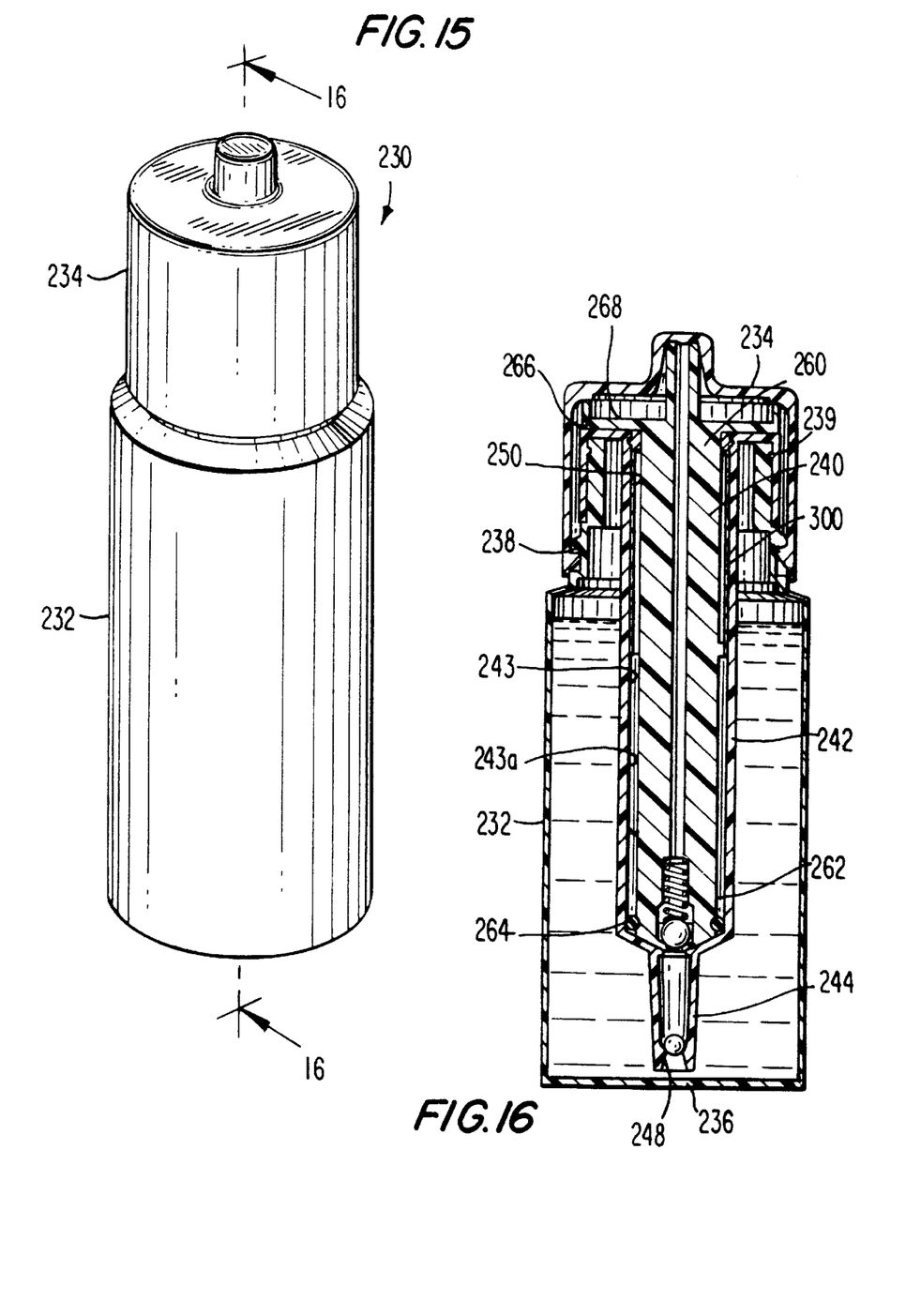
FIG. 15 is a perspective view of a liquid compliance package with programmable dosage constructed in accordance with another embodiment of the present invention.
FIG. 16 is a sectional view taken along line 16—16 of FIG. 15.

Bottle 232 includes a closed bottom 236 and an open neck 238. Cap 234 is removable from neck 238 and may be releasably secured thereto by a snap fit, threads or the like. It is also noted that cap 234 may be child resistant making it difficult for a child to remove cap 234 from bottle 232.

A dispenser apparatus shown generally at 240 is supported on neck 238. Dispenser apparatus 240 includes a hollow housing 242 having a first end 244 having an opening 248 and a second open end 250. A plunger device 260 extends into the hollow portion 243 of housing 242. A first end 262 of plunger device 260 includes an elastomeric seal or washer 264 which rides against inner wall 243a of hollow portion 243 of housing 242 so that liquid can be drawn into housing 242 through opening 248 as will be described in detail hereinafter.

Second end 266 of plunger device 260 includes an enlarged area or panel 268 which can be grasped, rotated and pulled longitudinally along housing 42 to operate the dispenser of this embodiment of the invention. Panel 268 includes a window 270 which is automatically selectively aligned with varying indicia 280 on a corresponding surface 252 of housing 242. Indicia 280 preferably represent an indication of the sequence or dosage to be dispensed or that has just been dispensed.

Figure 21:
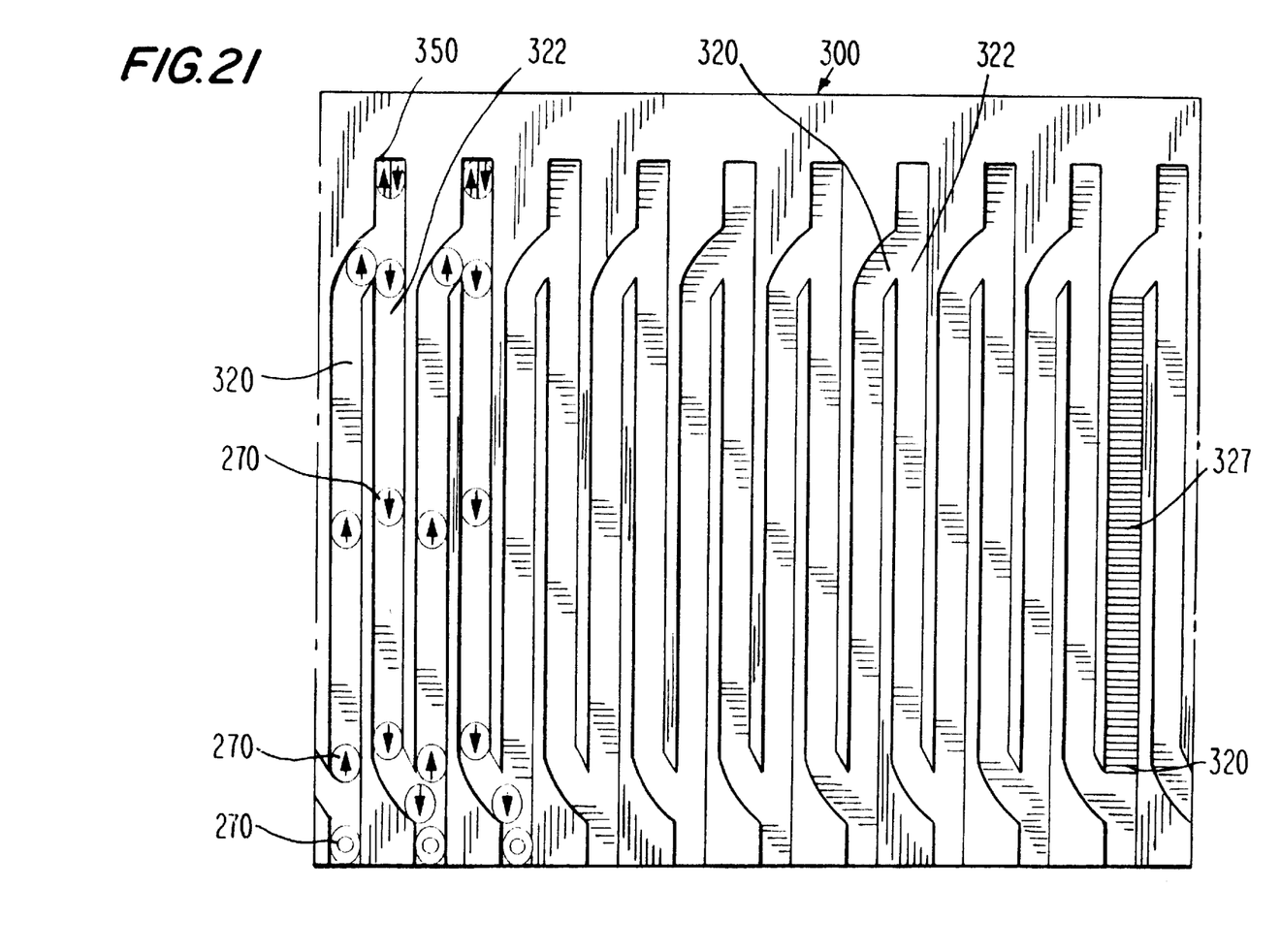
FIG. 21 is an enlarged layout view of the keyway or ramp construction in a flat configuration showing the general layout of a possible dosage and compliance program in accordance with the present invention.
Figures 22, 23, 24:
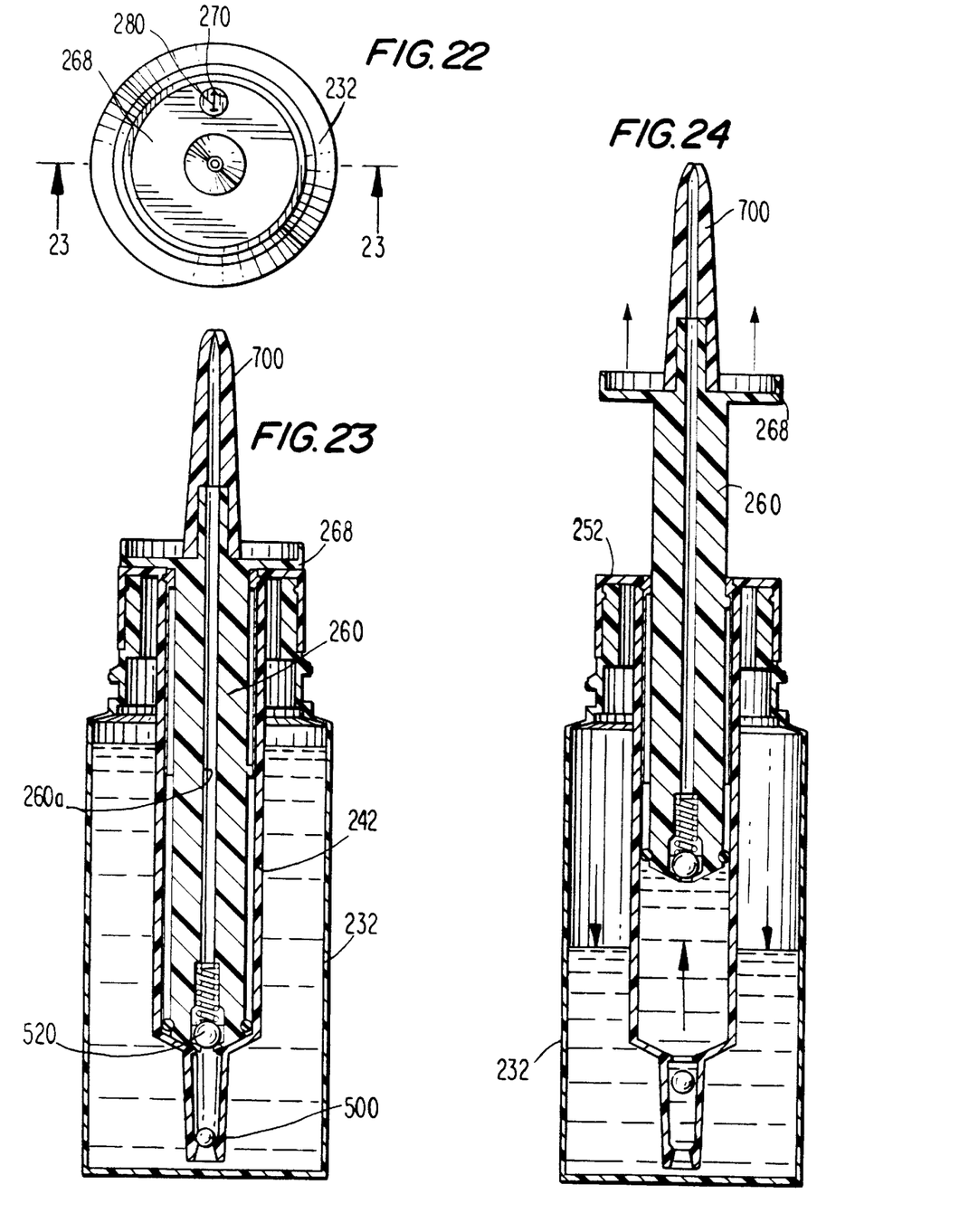
FIG. 22 is a top plan view of a spray dispenser constructed in accordance with an alternative embodiment of the present invention.
FIG. 23 is a sectional view taken along line 23—23 of FIG. 22.
FIG. 24 is a sectional view similar to FIG. 23 but showing the nozzle and plunger raised in preparation for dispensing.

A compliance cam and keyway design 300 is provided or formed on inner surface 243 of housing 242 as depicted. FIG. 21 depicts compliance cam and keyway design in detail. The device includes a plurality of back and forth interconnected passageways 320 and 322 in which a key or projection 270 on plunger device 260 rides as plunger 260 is moved longitudinally with respect to housing 242.

Compliance cam device 300 may be formed flat as shown in FIG. 21 and then rolled, inserted and fixed in housing 242, or it may be formed round, or it may be formed directly on the inner surface 243a of housing 242, or in other appropriate ways so long as a continuous trackway is provided.

Figures 17, 18, 19:
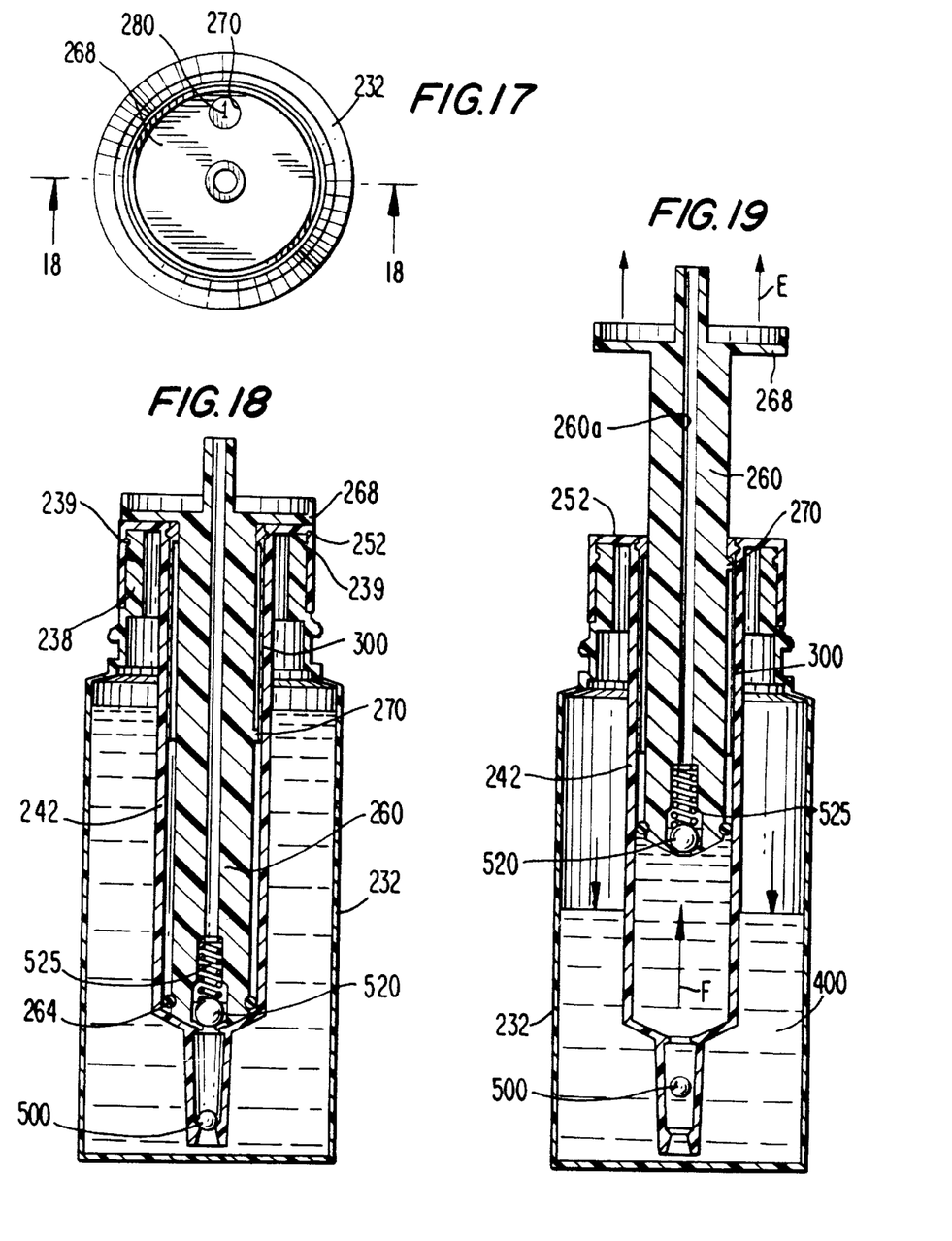
FIG. 17 is a top plan view of the package depicted in FIGS. 15 and 16 shown with the cap removed.
FIG. 18 is a sectional view taken along line 18—18 of FIG. 17.
FIG. 19 is a sectional view similar to FIG. 18 but showing the plunger in a raised position prior to product dispensing.

As shown in FIG. 21, when plunger 260 is in its lower position as depicted in FIG. 18, cam follower 270 is in its lower position as shown by the oval in FIG. 21 with the circle therein. At this time, the numeral 1 is visible through window 270 as depicted in FIG. 17 indicating that the device is in condition for dispensing the first dose of medicine. When plunger device 260 is pulled upwardly in the direction of arrow E as depicted in FIG. 19, liquid 400 will be drawn into housing 242. Cam follower 270 will move upwardly along passageway 320 in the direction of the oval up arrows in FIG. 21 until the top surface 350 of the first passageway is contacted. This will be the uppermost stroke action allowing housing to be filled with the predetermined dosage of liquid 400 represented by the length of this stroke.

Referring to FIGS. 18 and 19, it is noted that first end 244 of housing 242 includes a one way ball valve 500 therein while first end 262 of plunger device 260 includes a one way ball valve 520 biased downwardly by a spring 525. Plunger device 260 also includes a through passageway 260a. As plunger device 260 is moved upwardly in the direction of arrow E as depicted in FIG. 19, ball valve 500 will be displaced allowing liquid 400 to be drawn in the direction of arrow F into housing 242. Ball valve 520 and plunger device 260 remains closed under the bias of spring 525. As noted above, when cam follower 270 hits the top surface 350 of first passageway, longitudinal movement thereof will be stopped. Plunger device 260 is now ready for its downward stroke.

Figure 20:
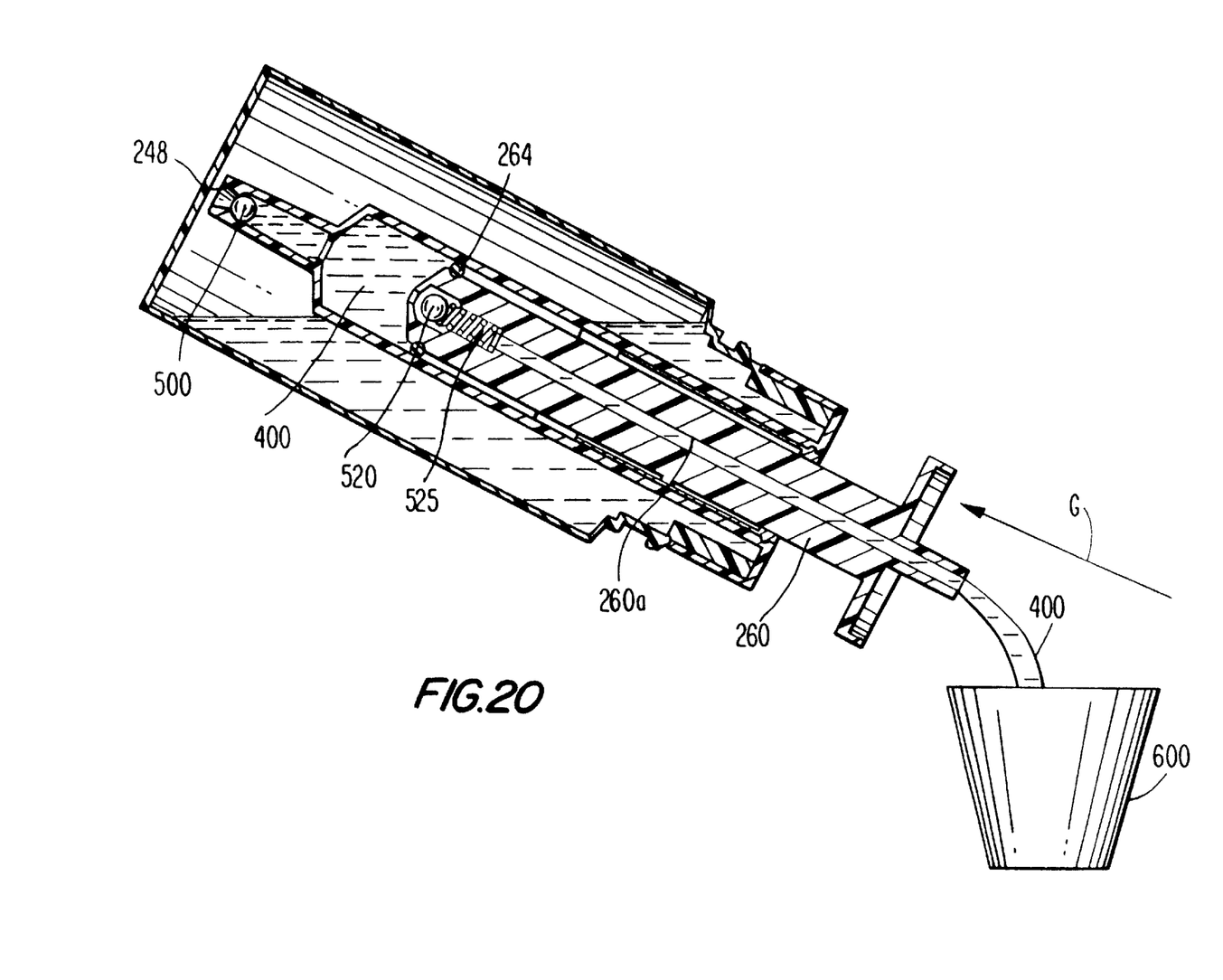
FIG. 20 is a sectional view showing dispensing of the liquid dosage as the plunger is depressed.

Referring to FIGS. 20 and 21, in particular, it is noted that when plunger device 260 is moved downwardly in the direction of arrow G, ball valve 500 will close off opening 248 and ball valve 520 will be forced open thereby causing liquid 400 to flow through passageway 260a out of plunger device 260 into a cup or other such device 600 for dispensing. Cam follower 270 will move downwardly in the direction of the down arrows in FIG. 21 along passageway 322 until the lower most position is reached. At this time, the plunger will have been slightly rotated so that window 270 is now aligned with a second indicia such as the numeral 2 to indicate that the device is ready to dispense dosage number two at the appropriate time.

It is noted that the length of each passageway 320 on the upward stroke may be selectively determined so that different dosages are provided for each different stroke of the plunger. It is also noted that since this embodiment utilizes a compliance package format, it may be desirable to have the dispenser apparatus fixed on neck 238 by using undercuts 239 or other such retention devices.

As representatively shown in FIG. 21, each upward passageway 320 may include means for preventing downward movement of the follower therealong, such as providing serrations 327 or the like. This will prevent partial dispensing of a required dosage since the full upward stroke would have to be made to allow the plunger to be pressed downwardly to dispense the product through the opening.

FIGS. 22 through 25 depict an embodiment of the present invention as applied to a spray type device to dispense precise amounts of mist or liquid, such as in the use of a nose spray or the like. Like parts in FIGS. 22 through 25 are numbered similarly to the corresponding parts depicted in FIGS. 17 through 20. The significant difference is that a nozzle 700 is placed over slot 260a which allows a mist 702 to be expelled as plunger device 260 is pressed downwardly in the direction of arrow H.

Figures 25, 26:
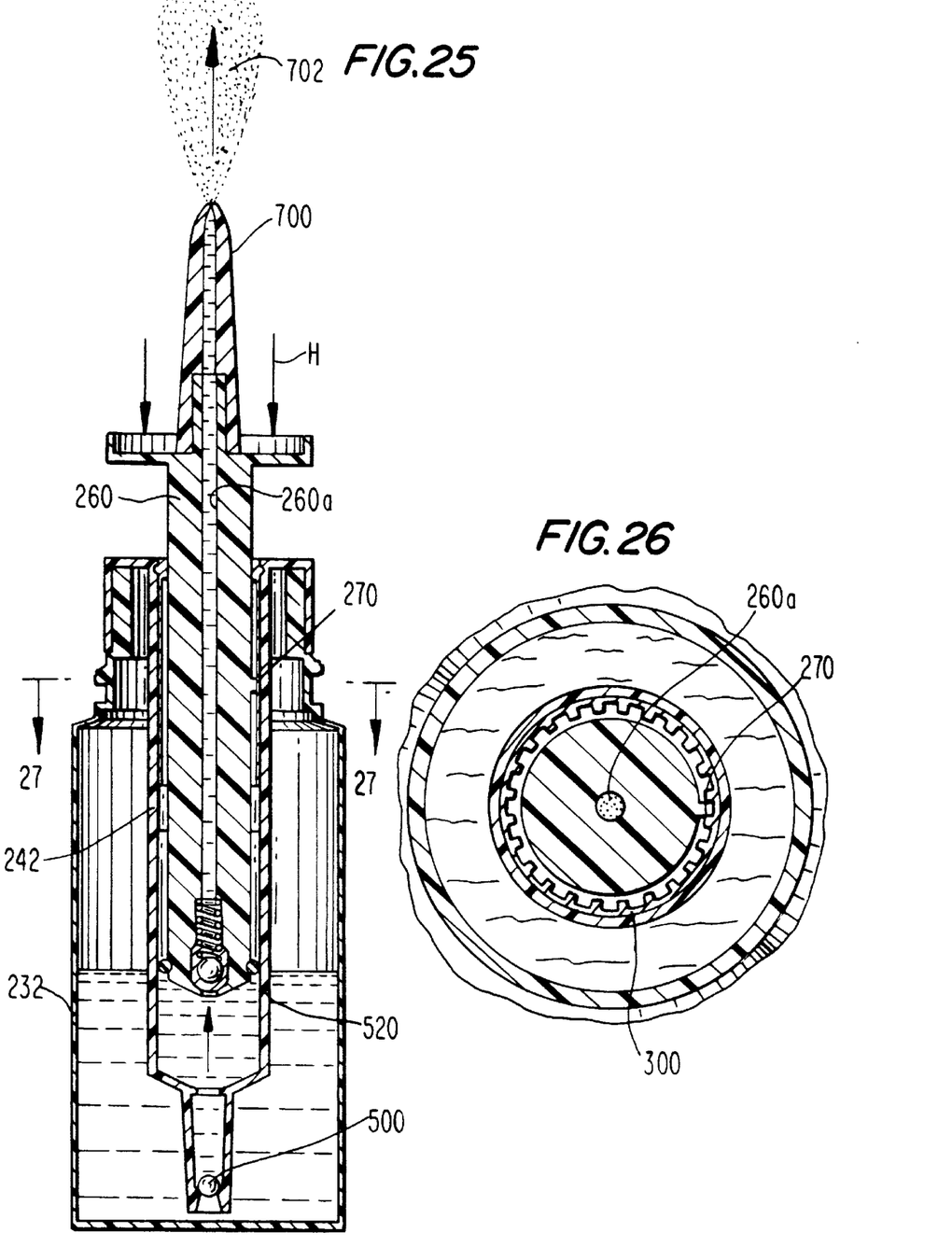
FIG. 25 is a sectional view showing product being released through the nozzle as the plunger is pressed downwardly.
FIG. 26 is a sectional view taken along line 26—26 of FIG. 25.

FIG. 26 depicts the compliance cam panel 30 in position on housing 242 with follower or key 270 positioned in one of the tracks.

The present invention as described above provides several different forms of liquid dosage packages which allow for precise and convenient dosage measurement. The devices are relatively easy and inexpensive to manufacture, and are easy to use.

It will thus be seen that the objects set forth above, among those made apparent from preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A liquid dosage dispenser comprising a bottle for containing a liquid, said bottle having an open neck, a dispenser apparatus supported on said neck having a housing extending into said bottle and a plunger device extending into said housing for longitudinal movement therein, said housing having an opening through which liquid in said bottle can be drawn into said housing, one of said housing and plunger device including stop means of predetermined configuration for stopping longitudinal movement of said plunger device and the other of said housing and plunger device including follower means for contacting said stop means, said plunger device being rotatable with respect to said housing to align said follower means with a desired portion of said stop means, said follower means and stop means, when aligned, allowing said plunger device to be moved longitudinally along said housing until said follower means contacts said stop means to draw a predetermined amount of liquid through said opening into said housing, said dispenser apparatus being removable from said bottle to permit said predetermined amount of drawn liquid to be dispensed through said opening, said stop means including an inclined ramp extending around said housing, said inclined ramp being positioned on said housing and said follower means being positioned on said plunger device, said follower means contacting a section of said ramp depending on the rotational position thereof to stop longitudinal movement of said plunger device with respect to said housing, said housing and plunger device including cooperating means to prevent rotation of said plunger with respect to said housing once said plunger has been displaced longitudinally.

2. The liquid dosage dispenser as claimed in claim 1, wherein said cooperating means are corresponding serrated surfaces on said housing and plunger devices.

3. A liquid dosage dispenser comprising a bottle for containing a liquid, said bottle having an open neck, a dispenser apparatus supported on said neck having a housing extending into said bottle and a plunger device extending into said housing for longitudinal movement therein, said housing having an opening through which liquid in said bottle can be drawn into said housing, one of said housing and plunger device including stop means of predetermined configuration for stopping longitudinal movement of said plunger device and the other of said housing and plunger device including follower means for contacting said stop means, said plunger device being rotatable with respect to said housing to align said follower means with a desired portion of said stop means, said follower means and stop means, when aligned, allowing said plunger device to be moved longitudinally along said housing until said follower means contacts said stop means to draw a predetermined amount of liquid through said opening into said housing, said dispenser apparatus being removable from said bottle to permit said predetermined amount of drawn liquid to be dispensed through said opening, said plunger device and said housing including cooperative indicia means for indicating the amount of liquid to be drawn into said housing as said plunger device is longitudinally displaced, said cooperative indicia means including a window on said plunger device and indicia on said housing.

4. The liquid dosage dispenser as claimed in claim 3, wherein when said window is aligned with a selected indicia, said follower means contacts a predetermined portion of said stop means during longitudinal displacement of said plunger device to draw the amount of liquid indicated by said selected indicia into said housing.

* * * * *